United States Patent
Vyas et al.

(10) Patent No.: US 11,692,913 B2
(45) Date of Patent: Jul. 4, 2023

(54) AIR CONSTITUENT MEASUREMENT SYSTEM, METHOD AND APPARATUS

(71) Applicant: Oizom Instruments Pvt. Ltd., Ahmedabad (IN)

(72) Inventors: Ankit Vyas, Ahmedabad (IN); Vrushank Vyas, Ahmedabad (IN); Sohil Patel, Ahmedabad (IN)

(73) Assignee: Oizom Instruments Pvt. Ltd., Ahmedabad (IN)

( * ) Notice: Subject to any disclaimer, the term of this patent is extended or adjusted under 35 U.S.C. 154(b) by 925 days.

(21) Appl. No.: 16/077,374

(22) PCT Filed: Feb. 13, 2017

(86) PCT No.: PCT/IN2017/050059
§ 371 (c)(1),
(2) Date: Aug. 10, 2018

(87) PCT Pub. No.: WO2017/138024
PCT Pub. Date: Aug. 17, 2017

(65) Prior Publication Data
US 2021/0270702 A1    Sep. 2, 2021

(30) Foreign Application Priority Data

Feb. 11, 2016  (IN) .............................. 201621002677

(51) Int. Cl.
*G01N 1/22* (2006.01)
*G01N 1/00* (2006.01)
*G01N 1/02* (2006.01)

(52) U.S. Cl.
CPC ............. *G01N 1/2205* (2013.01); *G01N 1/00* (2013.01); *G01N 1/02* (2013.01); *G01N 1/22* (2013.01);
(Continued)

(58) Field of Classification Search
CPC .. G01N 1/00; G01N 1/02; G01N 1/22; G01N 1/2205; G01N 1/2273; G01N 2001/222;
(Continued)

(56) References Cited

U.S. PATENT DOCUMENTS 3,408,869 A    11/1968  Auger
4,100,806 A *  7/1978  Carbonnelle ........ G01N 1/2258
                                                    73/864.31
(Continued)

FOREIGN PATENT DOCUMENTS

CN    103785265 A  *  5/2014
ES       2438625 A1 *  1/2014  ......... G01N 33/0004
(Continued)

OTHER PUBLICATIONS

International Search Report and Written Opinion of the International Searching Authority for corresponding International Application No. PCT/IN2017/050059, dated Feb. 11, 2016, 16 pages.

*Primary Examiner* — Daniel S Larkin
*Assistant Examiner* — Fatemeh Esfandiari Nia
(74) *Attorney, Agent, or Firm* — Ditthavong, Steiner & Mlotkowski (57) ABSTRACT

Air quality measurement system, method and apparatus are described. The air quality measurement system is also referred to as air constituent measurement system. Various air-quality parameters such as, for example, particulate matter, SO2, NO2, CO, O3, H2S, CO2, HCL, NH3, CH4, VOC etc. can be measured.

14 Claims, 10 Drawing Sheets

(52) U.S. Cl.
CPC . *G01N 2001/222* (2013.01); *G01N 2001/227* (2013.01); *G01N 2001/2282* (2013.01)

(58) Field of Classification Search
CPC ..... G01N 2001/227; G01N 2001/2282; G01N 2001/2288
See application file for complete search history.

(56) References Cited

U.S. PATENT DOCUMENTS

| | | | | |
|---|---|---|---|---|
| 10,018,551 | B2* | 7/2018 | Walls | G01N 15/1459 |
| 2012/0222478 | A1* | 9/2012 | Kanenari | B60C 23/0408 |
| | | | | 73/146.5 |
| 2013/0047704 | A1* | 2/2013 | Bae | G01N 1/2273 |
| | | | | 73/31.02 |
| 2013/0061692 | A1* | 3/2013 | Muresan | G01N 33/0031 |
| | | | | 73/863 |
| 2013/0174646 | A1* | 7/2013 | Martin | F24F 11/62 |
| | | | | 73/31.02 |
| 2013/0298642 | A1 | 11/2013 | Gillette, II | |
| 2014/0157864 | A1 | 6/2014 | Sundal et al. | |
| 2015/0323430 | A1* | 11/2015 | Weling | G01N 1/405 |
| | | | | 436/181 |
| 2016/0116405 | A1* | 4/2016 | Bertaux | G06T 19/003 |
| | | | | 356/338 |
| 2016/0238494 | A1* | 8/2016 | Chrin, II | G01N 33/0073 |
| 2018/0143105 | A1* | 5/2018 | Kim | G01N 1/22 |
| 2018/0306681 | A1* | 10/2018 | Sekine | C12M 41/14 |

FOREIGN PATENT DOCUMENTS

| | | | | | |
|---|---|---|---|---|---|
| JP | 2011013157 | A | * | 1/2011 | |
| KR | 20120025036 | A | * | 3/2012 | |
| KR | 20160123762 | A | * | 4/2015 | |
| WO | WO-2007103793 | A2 | * | 9/2007 | ........... G01N 1/2202 |

* cited by examiner

AIR CONSTITUENT MEASUREMENT SYSTEM, METHOD AND APPARATUS

CROSS-REFERENCES TO RELATED APPLICATIONS

This application claims priority from PCT Application Serial No. PCT/IN2017/050059, entitled "Air Constituent Measurement System, Method and Apparatus," filed on Feb. 13, 2017, which claims priority from an Indian Application Serial No. 201621002677, filed on Feb. 11, 2016, the contents of which are hereby incorporated herein in their entirety by this reference.

BACKGROUND

A. Technical Field

The present invention relates generally to air quality measurement.

B. Background of the Invention

Air quality has a significant effect on the well being of living and non-living matter in an area. With increasing awareness on the ill effects caused by poor quality air there are numerous steps being taken by governments, institutions as well as individuals to address the problem.

In order to keep a check on the element/s causing the quality to deteriorate and take a corrective action measurement systems are needed.

The measurement of the air quality is an important step in keeping a check on elements that cause the quality to deteriorate. Depending on the constituent elements either a preventive or corrective action can be taken.

Available air-quality monitoring systems are predominantly divided into two types. Conventional Pollutant collection based mechanical experimental, and sensor based air-quality monitoring systems. The sampling based system usually takes an hour to a few hours for measurement. Since there is usually a considerable delay between collection and final result availability, the resulting numbers may not represent the air quality at that instance. Sensor based air-quality monitoring system on the other hand provides near real-time (current) data but is affected by the outside environmental factors like temperature, humidity, radio-waves, electromagnetic field, wind-speed, wind-direction, barometric pressure, air-turbulence etc. to name a few. The environmental factors affect the working principles of different sensors used and hence the accuracy of the measurement is affected.

There is therefore a need for air quality measurement system, method and apparatus that enables current air quality measurement while providing high level of accuracy.

SUMMARY OF THE INVENTION

An air constituent measurement apparatus is provided. The air constituent measurement apparatus includes a gas measurement chamber, an inlet separator for the gas measurement chamber configured to intermittently control the flow of surrounding air into the gas measurement chamber, atleast one real-time gas sensor configured to measure a constituent of Inlet air, an outlet separator for the gas measurement chamber configured to intermittently control the flow of the Inlet air into the surroundings, a particulate measurement chamber, an inlet separator for the particulate measurement chamber configured to intermittently control the flow of surrounding air into the particulate measurement chamber, atleast one real-time particulate sensor configured to measure a constituent of Inlet air and an outlet separator for the particulate measurement chamber configured to intermittently control the flow of the Inlet air into the surroundings.

An air conditioning system configured to maintain the temperature and humidity of the Inlet air in the measurement chamber is also provided within the air constituent measurement apparatus. A filtration mechanism in the gas measurement chamber is configured to filter particulates from entering the gas measurement chamber. Further, a protective coating for reducing the effect of electromagnetic and radio waves in the measurement chamber is provided. Furthermore, an inner coating reduces the inlet of fumes into the gas measurement chamber and the particulate measurement chamber. These fumes are usually emitted from the material used in the construction of the apparatus such as for example the plastic or fiber material used for construction of apparatus body.

BRIEF DESCRIPTION OF THE DRAWINGS

Reference will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments.

DETAILED DESCRIPTION OF THE PREFERRED EMBODIMENTS

Air quality measurement system, method and apparatus are described. The air quality measurement system is also referred to as air constituent measurement system in this specification. Various air-quality parameters such as, for example, particulate matter, $SO_2$, $NO_2$, $CO$, $O_3$, $H_2S$, $CO_2$, $HCL$, $NH_3$, $CH_4$, VOC etc. can be measured.

In the following description, for purpose of explanation, specific details are set forth in order to provide an understanding of the invention. It will be apparent, however, to one skilled in the art that the invention may be practiced without these details. One skilled in the art will recognize that embodiments of the present invention, some of which are described below, may be incorporated into a number of different air quality analysis systems and devices. The embodiments of the present invention may be present in hardware, software or firmware. Structures and devices shown below in block diagram are illustrative of exemplary embodiments of the invention and are meant to avoid obscuring the invention. Furthermore, connections between components within the figures are not intended to be limited to direct connections. Rather, data between these components may be modified, re-formatted or otherwise changed by intermediary components.

Reference in the specification to "one embodiment" or "an embodiment" means that a particular feature, structure, characteristic, or function described in connection with the embodiment is included in at least one embodiment of the invention. The appearances of the phrase "in one embodiment" in various places in the specification are not necessarily all referring to the same embodiment. Further, the use of "measurement" is not necessarily limited to a single act of measurement or reading but may refer to multiple such instances or readings. The headings and subheadings used in the document are not intended to limit the content therein to respective heading or subheading. Rather, they are used to help reader navigate and prevent obscuring the invention. References to air quality measurement also mean references to air constituent measurement.

A. Overview

Figure 1:
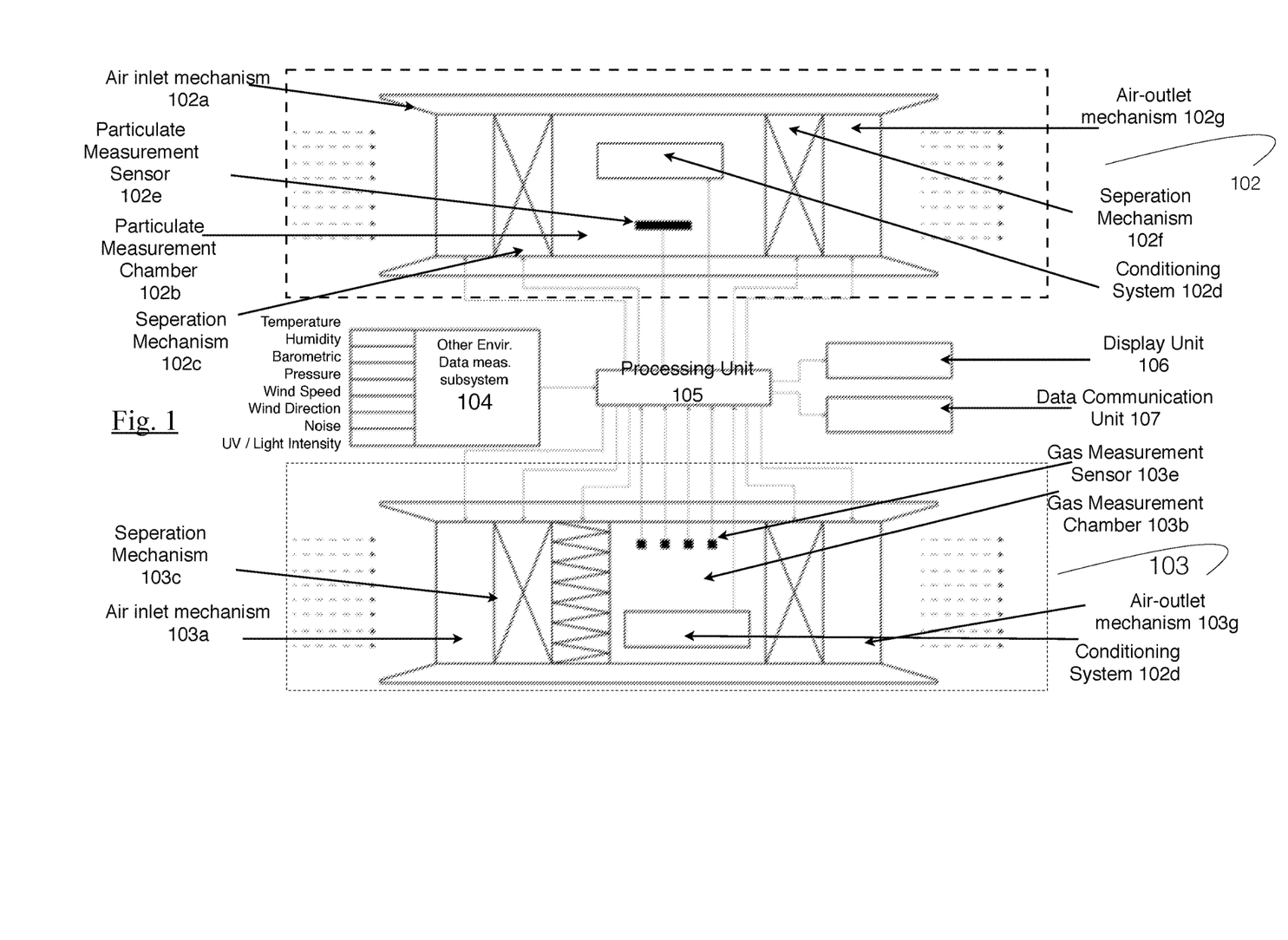
FIG. 1 illustrates a schematic of an air quality measurement system as per an embodiment herein.

FIG. 1 illustrates air quality measurement system 100 as per an embodiment herein. The system 100 is subdivided into particulate measurement subsystem 102 and gas measurement subsystem 103, other environmental data measurement subsystem 104, a processing unit 105, a display unit 106 and a data communication unit 107. In one embodiment as shown in FIG. 1, the gas measurement subsystem and the particulate measurement subsystem might be present separate from each other in such a way that each uses separate air samples for measurement. This division provides for increased accuracy by preventing settling of particulate matters on electronic components and sensors being used for gas measurement. The settled particles are generally known to deteriorate the life of electronic components and sensors. In another embodiment however, the gas and particulate measurements may be taken in a single chamber without isolating one from the other.

B. The Particulate Measurement Subsystem

The particulate measurement subsystem 102 consists of an air inlet mechanism 102a that provides for allowing air that needs to be measured brought into the particulate measurement subsystem. Various implementations of the air inlet mechanism may be used, some of which are disclosed in the specification.

The inlet-air may be made available in a particulate measurement chamber 102b. A separation in form of an inlet separator 102c may be provided for allowing separation of surrounding air and the inlet air. The separation in some embodiments may be momentarily active while in other embodiment may exist for a longer duration of time. The choice of separation and the time for which it remains active may depend on factors such as for example working principles of the particulate/gas measurement sensor, application/location of the measurement i.e. industrial application (lower separation time), smart city (more separation time), smart waste management etc. and environmental condition i.e. polluted environment is possible to measure with lower separation time particulate sensor type, the location of the measurement and the environment.

In one embodiment an inlet-air conditioning system 102d is provided to maintain temperature and humidity under desirable limits for improving the accuracy of particulate measurements. In one embodiment, modifying the humidity is achieved using humidification or dehumidification and the temperature is maintained by a temperature control element that heats or cools the inlet-air.

A particulate measurement sensor 102e is used to measure the levels of particulate matter inside the particulate measurement chamber 102b. Particulate measurement sensor 102e may consist of various sensors working on different principles like for example, laser scattering, NDIR, electrochemical, semiconductor, Ultraviolet Fluorescence, Chemiluminescence, Ultraviolet Absorption, Gas Filter Correlation, β Ray Absorption etc. The time taken (T) by measurement sensor for measurement depends on the types of parameters to be identified and accuracy of measurement to be achieved for example: For measurement of PM1 (Particulate Matters Less than 1 micron) in household indoor for high accuracy time taken (T) can be more, where for measurement of PM10 in city ambient condition time take (T) can be less. The sensors may be real time or near real time. The particulate measurement sensor may take multiple rounds of measurement of the inlet air depending on the working principle of the sensors and clock speed of the electronic system.

T=definite time period for a cycle of measurement.

R=rate of sampling based on working principle of the sensor and clock speed of the electronic system C=sensor reading of a particular air-quality parameter $$C=C0, C1, C2, C3, \ldots Cn \text{ where } n=R \times T$$

The measured readings of the particulate sensor are processed to achieve a final measurement of the particulate measurement. In one example the final measurement may be an average of the number of readings taken. In other embodiment the final measurement may be weighted average.

Another separation in form of an outlet separator 102f may be used for separating the Inlet-air and the surrounding air towards the exit of air path to provide isolation of the inlet air during measurement. The outlet separator 102f in some embodiments may be momentarily active while in other embodiment may exist for a longer duration of time.

An air outlet mechanism 102g aids in letting inlet-air out into surrounding air. Various implementations of the air outlet mechanism may be used, some of which are disclosed later in the specification.

C. The Gas Measurement Subsystem

The gas measurement subsystem 103 consists of an air inlet mechanism 103a that provides for allowing air that needs to be measured brought into the gas measurement subsystem. Various implementations of the air inlet mechanism may be used, some of which are disclosed in the specification.

Dust particles and suspended particulates impact the accuracy of the working of various sensors used for gas measurements, as well as their life. Hence, the inlet air may be filtered before entering a gas measurement chamber used for measurement of the gases. In one embodiment a filtration mechanism 103k may be used between the air inlet mechanism 103a and the gas measurement chamber 103b. In another embodiment the filtration may be performed even before it reaches the air inlet mechanism. A separation in form of an inlet separator 103c is provided for allowing separation of surrounding air and the inlet air. The separation in some embodiments may be momentarily active while in other embodiment may exist for a longer duration of time. The choice of separation and the time for which it remains active may depend on factors such as for example particulate sensor type, the location of the measurement and the environment.

In one embodiment an inlet-air conditioning system 103d is provided to maintain temperature and humidity under desirable limits for improving the accuracy of the measurements. In one embodiment, modifying the humidity is achieved using humidification or dehumidification and the temperature is maintained by a temperature control element that heats or cools the inlet-air.

Various gases related measurements may be performed using gas measurement sensor 103e. In one embodiment various sensors may be used for measurements related to different gases. In another embodiment the gas measurement sensor 103e may be present as a single unit. Gas measurement sensor 102e may consist of various sensors working on different principles like, for example, laser scattering, NDIR, electrochemical, semiconductor, Ultraviolet Fluorescence, Chemiluminescence, Ultraviolet Absorption, Gas Filter Correlation, β Ray Absorption etc. The sensors may be real time or near real-time. The time taken (T) by measurement sensor for measurement depends on the types of parameters to be identified and accuracy of measurement to be achieved for Example: For measurement of volatile organic compounds (VOC) in indoor household condition time taken (T) can be more, where in case of measurement of VOC in ambient condition of an industrial site time taken (T) can be less. The gas measurement sensor may take multiple rounds of measurement of the inlet air depending on the working principle of the sensors and clock speed of the electronic system.

T=definite time period for a cycle of measurement.
R=rate of sampling based on working principle of the sensor and clock speed of the electronic system
C=sensor reading of a particular air-quality parameter $$C=C0,C1,C2,C3,Cn \text{ where } n=R \times T$$

The measured readings of the gas sensor are processed to achieve a final measurement of the particulate measurement. In one example the final measurement may be an average of the number of readings taken. In other embodiment the final measurement may be weighted average.

Another separation in form of an outlet separator 103f may be used for separating the Inlet-air and the surrounding air towards the exit of air path to provide isolation of the inlet air during measurement. The Separation 103f in some embodiments may be momentarily active while in other embodiment may exist for a longer duration of time.

An air outlet mechanism 103g aids in letting the inlet-air out into the surrounding air. Various implementations of the air outlet mechanism may be used, some of which are disclosed in other parts of the specification.

D. Other Environmental Data Measurement Subsystem

Environmental factors effect the air-quality measurement and are used to analyze, calibrate or recalibrate the measurement related with the particulate measurement as well as the gas measurement.

The other environmental data measurement subsystem comprises of various sensors to measure environmental factors such as, for example, temperature, humidity, barometric pressure, Wind Speed, Wind Direction, Noise, UV/Light Intensity. A person skilled in the art may recognize that the above list is not exhaustive and some other environmental factors may be added and some of these environmental factor measurement sensors may be avoided depending on nature of installment.

E. Processing Unit

A processing unit 105 may be provided communicatively coupled to the particulate measurement subsystem 102, the gas measurement subsystem 103 and the other environmental data measurement system 104. The processing unit may process various measurement data. In one embodiment, the processing unit may include calibration information related with various measurements from the particulate sensor and gas sensor.

In one embodiment a display unit 106 may also be provided that shows various measurements comprising particulate measurement, gas measurement and a collective air-quality measurement. The display unit is communicatively coupled to the processing unit 105.

Further, a data communication unit 107 may also be provided to enable communication of the air quality measurements. The communication unit may also be used to remotely program the processing unit or for calibration of various measurement sensors. In some instances the communication may be local and in others may be communicated to a central server. Details of various such implementations are disclosed in other parts of the specification.

F. System Construction

Figure 2:
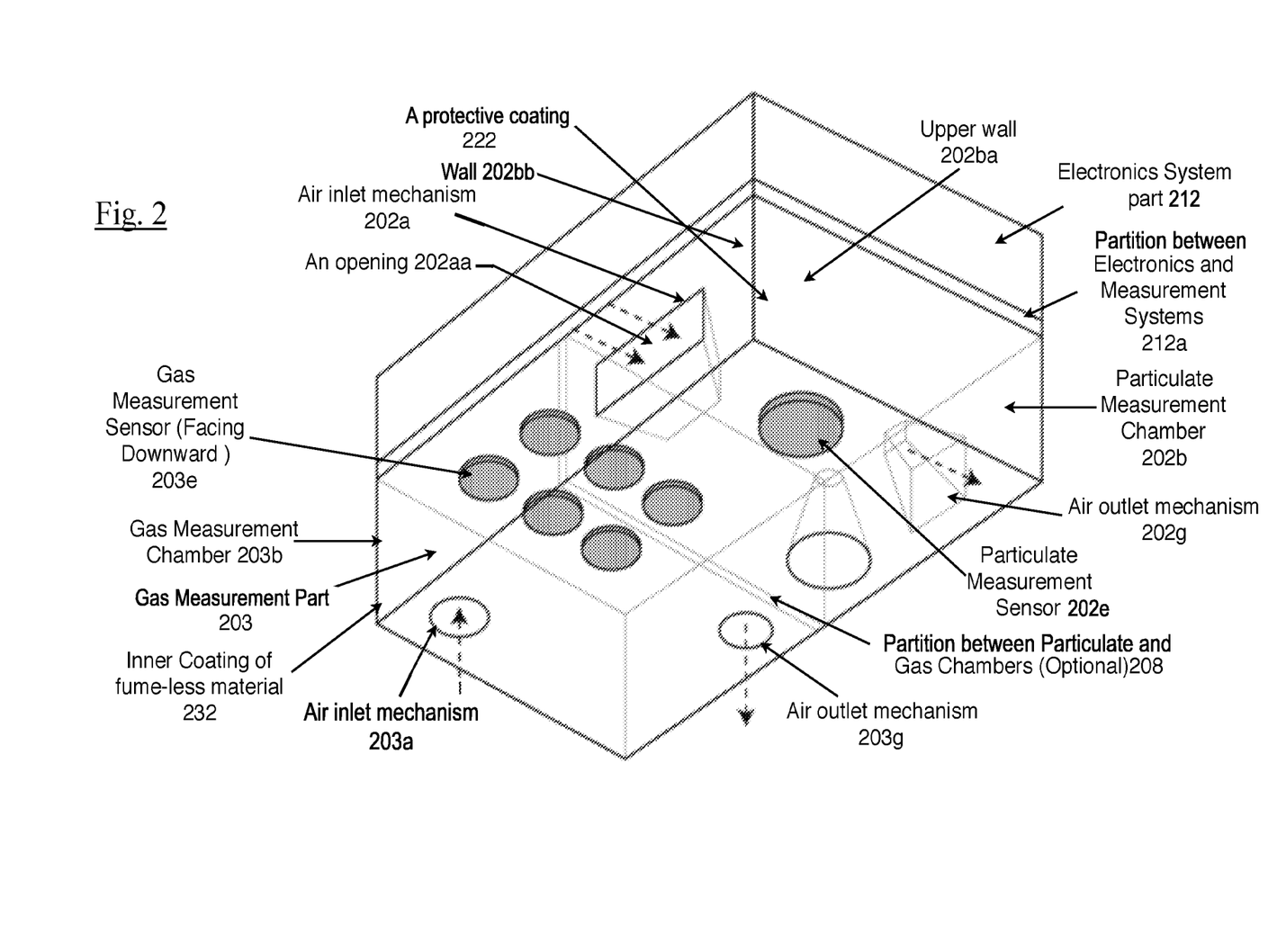
FIG. 2 illustrates an air quality measurement system as per an embodiment herein.

FIG. 2 shows an apparatus embodying the air quality measurement system of FIG. 1, as per an embodiment herein. The apparatus comprises of a particulate measurement part 202 and a gas measurement part 203. An electronics system part may be provided over the particulate and gas measurement parts. In one embodiment the electronics system part may be isolated with the help of an electronics system partition 212a. In one embodiment a partition 208 between the particulate measurement part and the gas measurement part may be provided. In another embodiment the partition may be absent. An air inlet mechanism 202a may consist of an opening 202aa on the wall 202bb. The opening gradually reduces in area providing for narrower opening into a particulate measurement chamber 202b. This causes venturi effect. In one embodiment the opening may be rectangular. Other shapes may also be used. The three-dimensional shape thus formed provides for natural separation of surrounding air and the inlet-air. A particulate measurement sensor 202e may be placed on the upper wall 202ba. An air outlet mechanism 202g may be provided with an opening 202ga. The opening gradually increases in area providing for reverse venturi effect.

The gas measurement part comprises of air inlet mechanism 203a for the gas chamber and a separation 203c allowing air into the gas measurement chamber. In one embodiment a fan arrangement with a circular opening 203aa may be provided. An air outlet mechanism 203g for the gas chamber may also be provided with an opening 203ga.

The construction of the apparatus provides for stable conditions during the measurements. A protective coating 222 on inner surface throughout the apparatus may be provided to avoid radio-wave/electromagnetic interference. Exemplary materials that may be used include highly-filled polymer-carbon composites, Nickel Copper Fabric Layer, PVC colloidal graphite composite, PVC graphene composite, PVC acetylene black composite. Further, an inner coating 232 of fume-less material such as for example Stainless steel 316, Teflon, Glass, Polytetrafluoroethylene, may be provided along the inner surface of gas measurement chamber.

Figure 3:
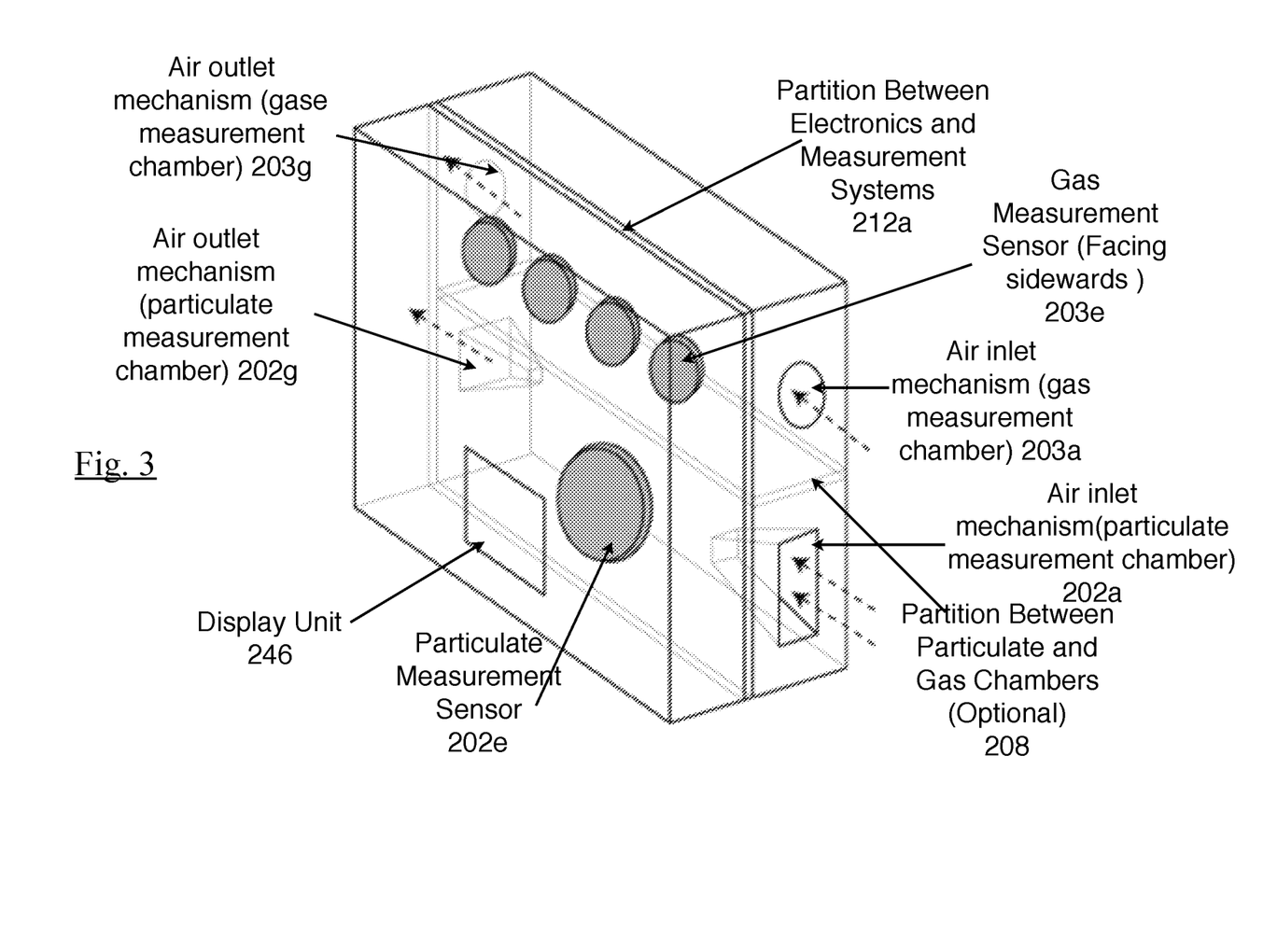
FIG. 3 illustrates an air quality measurement system as per an embodiment herein.

The basic construction of the air quality measurement system as explained may be modified depending on the application. For example, in case of indoor application a construction as shown in FIG. 3 may be used. As shown in this exemplary embodiment, a display unit 346 may be provided that allows quick access to the value of measured parameters. The display unit may be replaced or provided in combination with a control unit (not shown) to allow user access to system settings, troubleshooting and control. This exemplary construction provides for flow path that is comparatively linear as compared to that shown in FIG. 2. For example, the airflow-path in the gas measurement chamber now allows for comparatively linear flow from air inlet mechanism 303a to air outlet mechanism 303g. The gas measurement sensors 303e are attached on a vertical wall of electronics system partition 312a. The particulate measurement sensor 302e is also provided in a vertical orientation attached to the electronics system partition 312a.

G. Measurement Chamber Construction

Numerous other constructions of the measurement chambers used for gas measurement and particulate measurement can be used. One such construction is as shown in exemplary embodiment of FIG. 4. In this embodiment, a measurement chamber may be provided having an axis coinciding with a shaft 444. The measurement chamber may be cylindrical in one embodiment.

Figure 4:
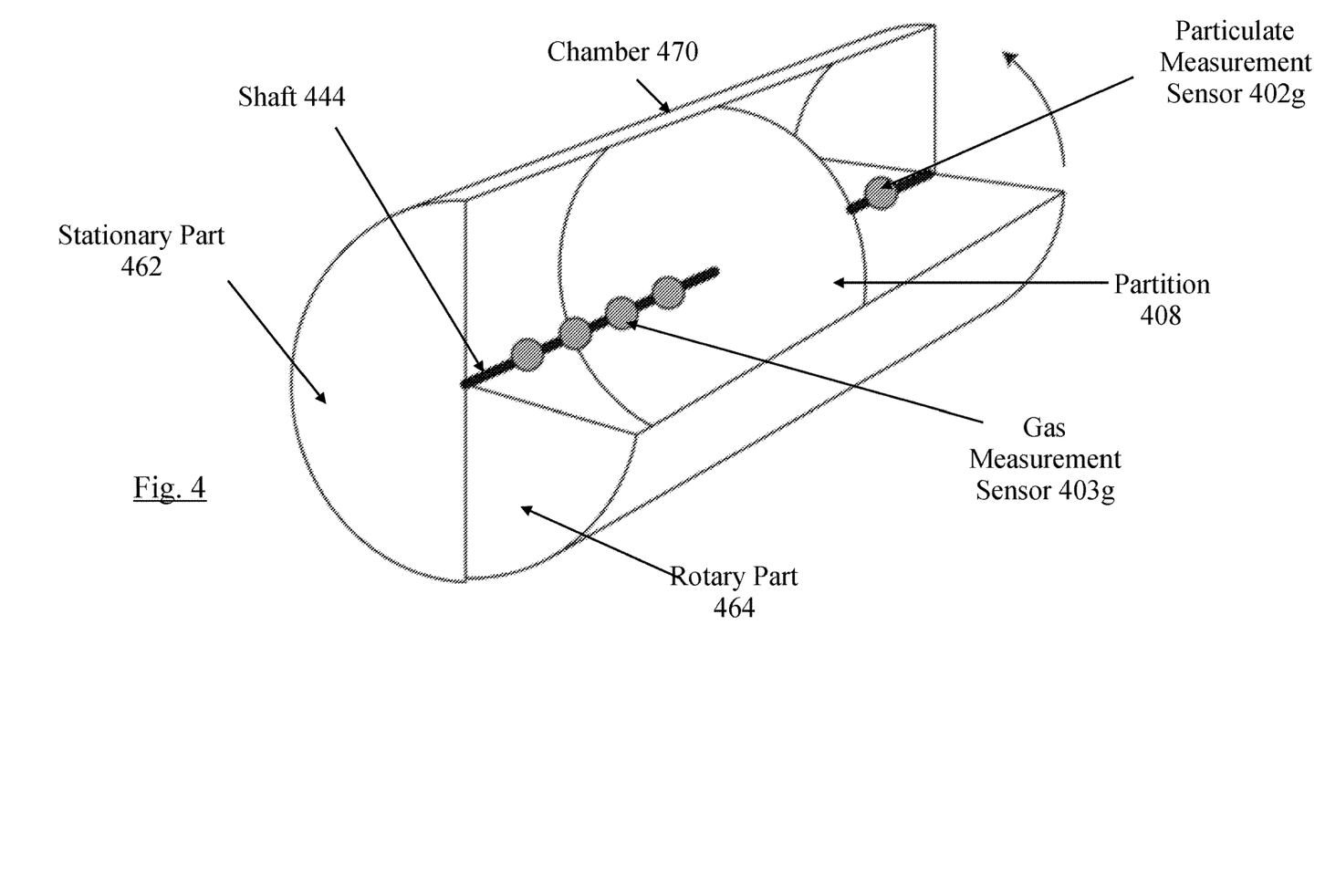
FIG. 4. Illustrates a measurement chamber construction as per an embodiment herein.

A stationary part may be provided having atleast some portion of the shaft in the stationary part. A rotary part 464 may be provided rotatable along the shaft 444. The rotary part and the stationary part may be in form of a cylindrical section cut along the axis of the cylinder. In one embodiment a partition 408 may be present allowing for isolation of air used for gas measurement and particulate measurement. In another embodiment no such partition is made available. This partition when present may be in form of a disc on the shaft 444. Gas measurement sensors 403g and particulate measurement sensor 402g may be placed on the shaft. The shaft 444 may also house electronic circuitry. In one embodiment the wiring may be run from in between the shaft and connected with other electronic circuitry outside the measurement chamber 470.

The rotary part may be made to rotate along the axis of shaft 444. This allows for inlet of fresh air into the measurement chamber 470. The speed of rotation or closing and opening may be varied depending on the time taken (T) for the measurement which in turn depends on the types of parameters to be identified and accuracy of measurement to be achieved for Example: For measurement of PM1 (Particulate Matters Less than 1 micron) in household indoor for high accuracy time taken (T) can be more, where for measurement of PM10 in city ambient condition time take (T) can be less. The particulate measurement sensor and gas measurement sensors may take multiple rounds of measurement of the inlet air depending on the working principle of the sensors and clock speed of the electronic system.

The frequency at which fresh air is introduced into the measurement chamber may be similar for gas as well as the particulate measurement subsystem. In order to provide for separate cycles two separate cylindrical chambers may be provided (not shown in the figure) that may rotate at different speeds with respect to each other. This may be provided on a common shaft or separate shaft.

Figure 5:
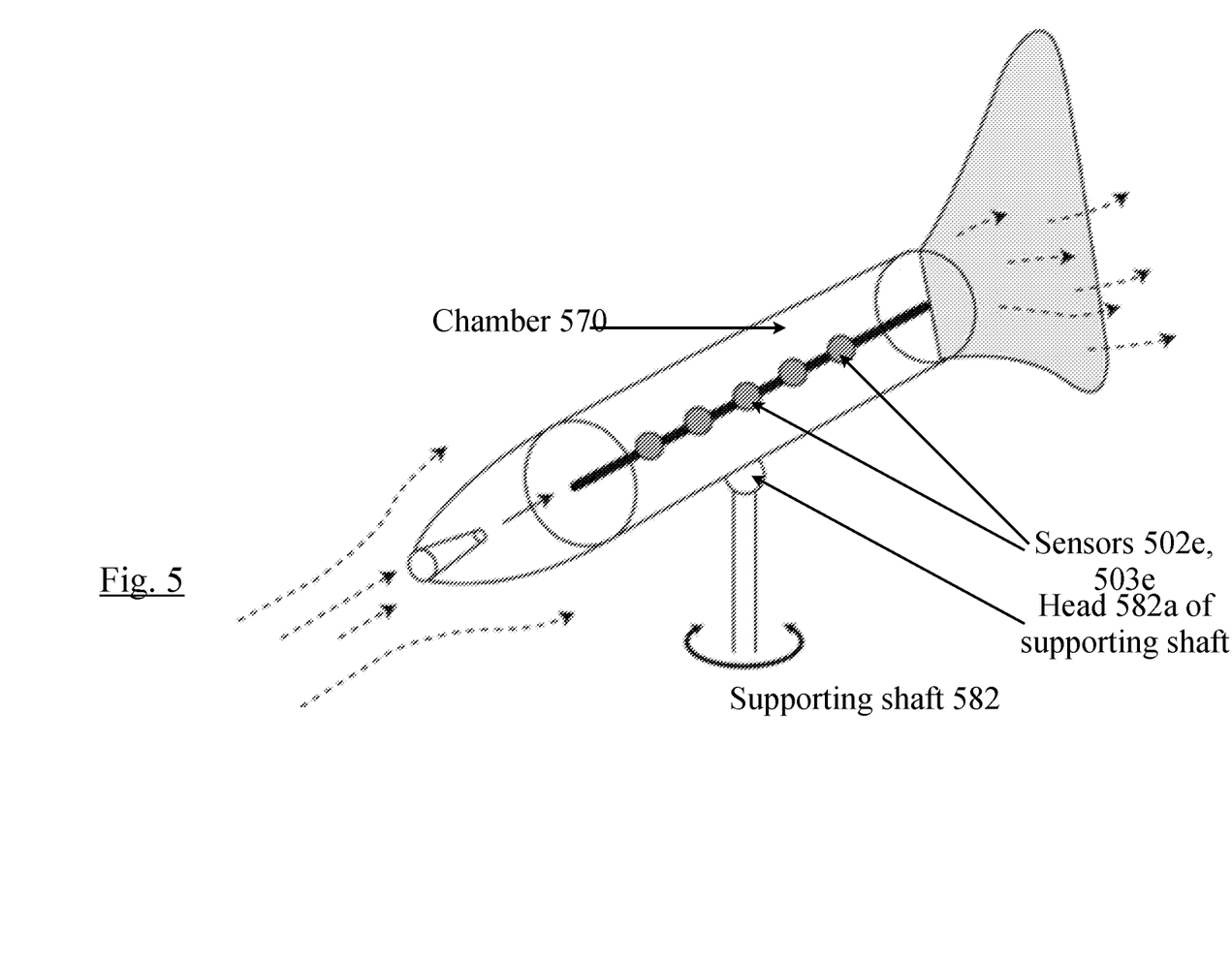
FIG. 5 illustrates a measurement chamber construction as per an embodiment herein.

Another construction of the measurement chamber as per an embodiment is as shown in FIG. 5. In this exemplary embodiment a measurement chamber 570 may be provided having a venturi shaped head. The measurement chamber may be cylindrical in one embodiment. Other shapes may also be used. A shaft 544 may run through the measurement chamber 570. Various sensors (502e, 503e) may be placed on the shaft. The measurement chamber may be placed on a supporting shaft 582. The supporting shaft is rotatable upto 360 degrees along the axis of the support shaft. The head 582a may be provided to have varying degrees of freedom. A pin joint allowing varying degrees of freedom may be provided when the supporting shaft attaches to the measurement chamber.

H. Housing Assembly

Figure 6:
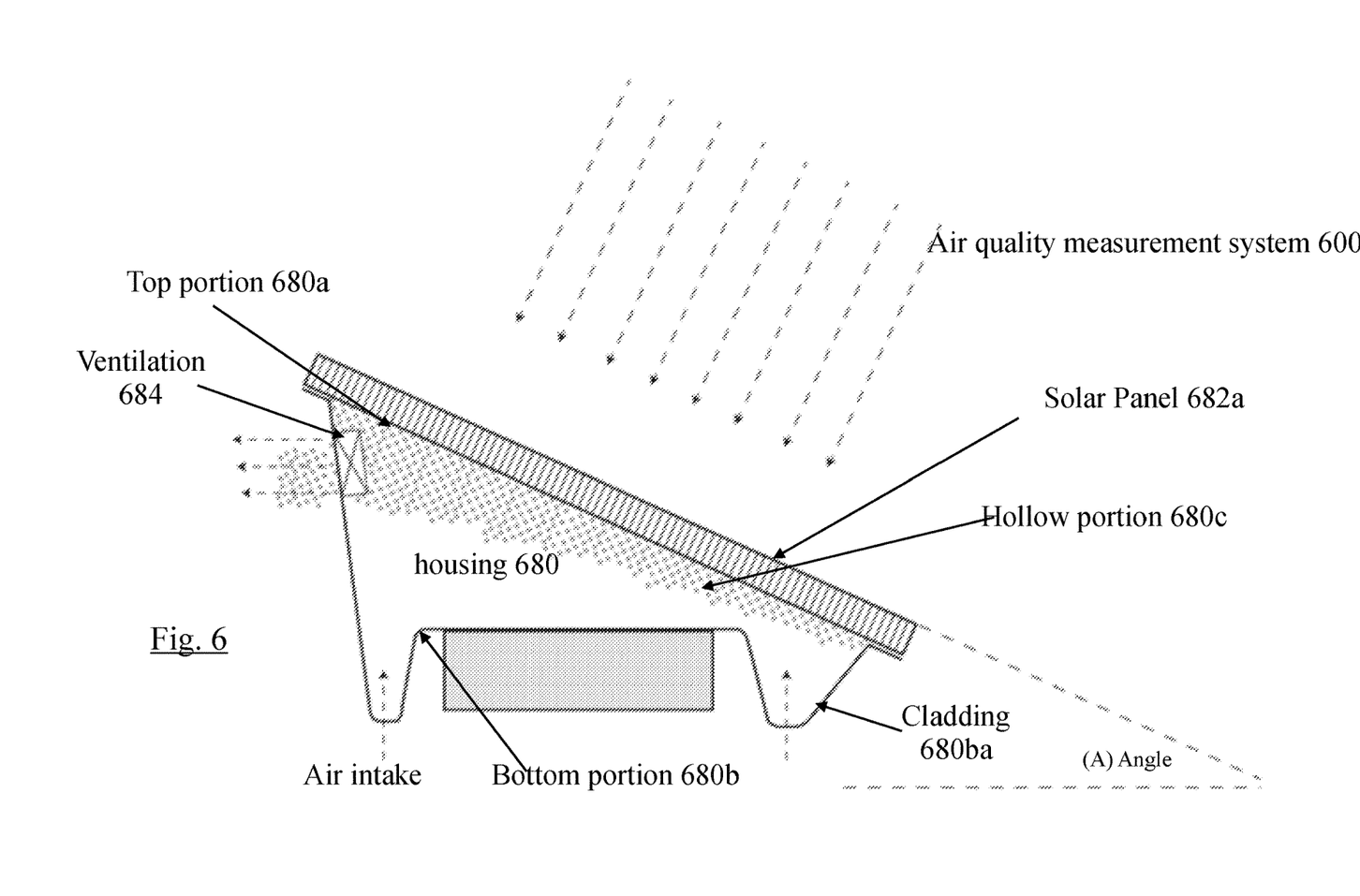
FIG. 6 illustrates side view of a housing with the air-quality measurement system as per an embodiment herein.
Figure 7:
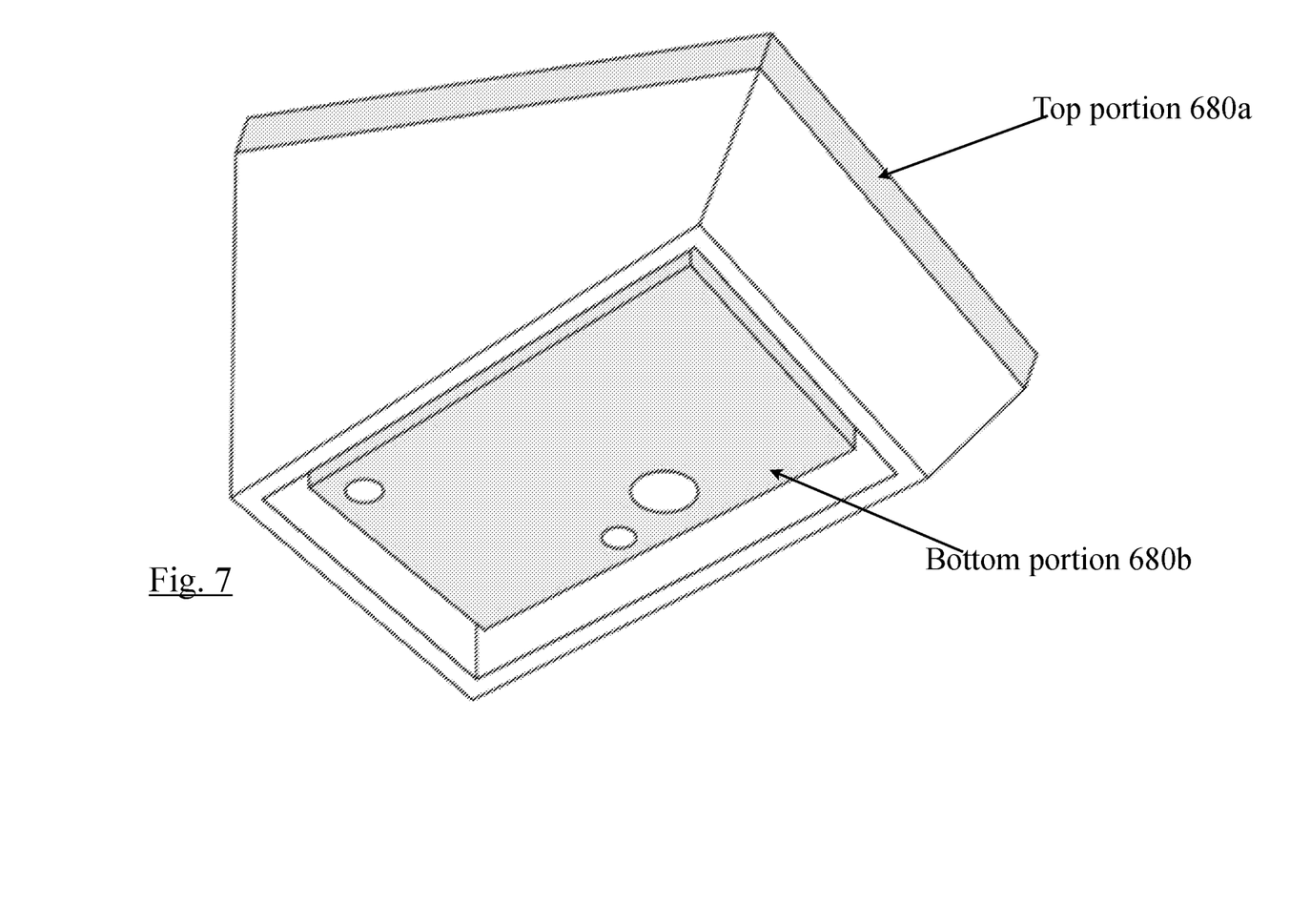
FIG. 7 illustrates an isometric view of a housing with the air-quality measurement system as per an embodiment herein.

Depending on the place of deployment of the air quality measurement system various housings may be required. One such housing 680 as per an embodiment herein is as shown in FIG. 6. In this embodiment the housing may provide for placement of the air quality measurement system under the housing. This allows for access of air for the air quality measurement system from the bottom portion 680b of the housing.

The top portion 680a of the housing may comprise of a top surface 682 having solar panels 682a fixed thereon. The top surface 689 may be inclined at an angle with respect to the bottom portion 680b, where the air quality measurement system may be fixed. The angle may vary depending on the sun direction for maximum power generation for the measurement apparatus. The housing may be hollow and may provide for an insulation effect protecting electronic circuitry from excessive heat. The hollow portion 680c may be used for back-up battery, charging circuits, processing and communication unit. The hollow portion 680c also provides for natural thermal separation for solar panels 682a and the air quality measurement system 600. The air in the hollow portion would rise and be concentrated along the top portion of the housing. Ventilation 684 may be provided to allow exit path for the heated air.

The bottom portion 680b of the housing may include cladding 680ba providing protection against water drops or mist. It also provides for protection of the air quality measurement system against wind.

I. Ecosystem

Figure 8:
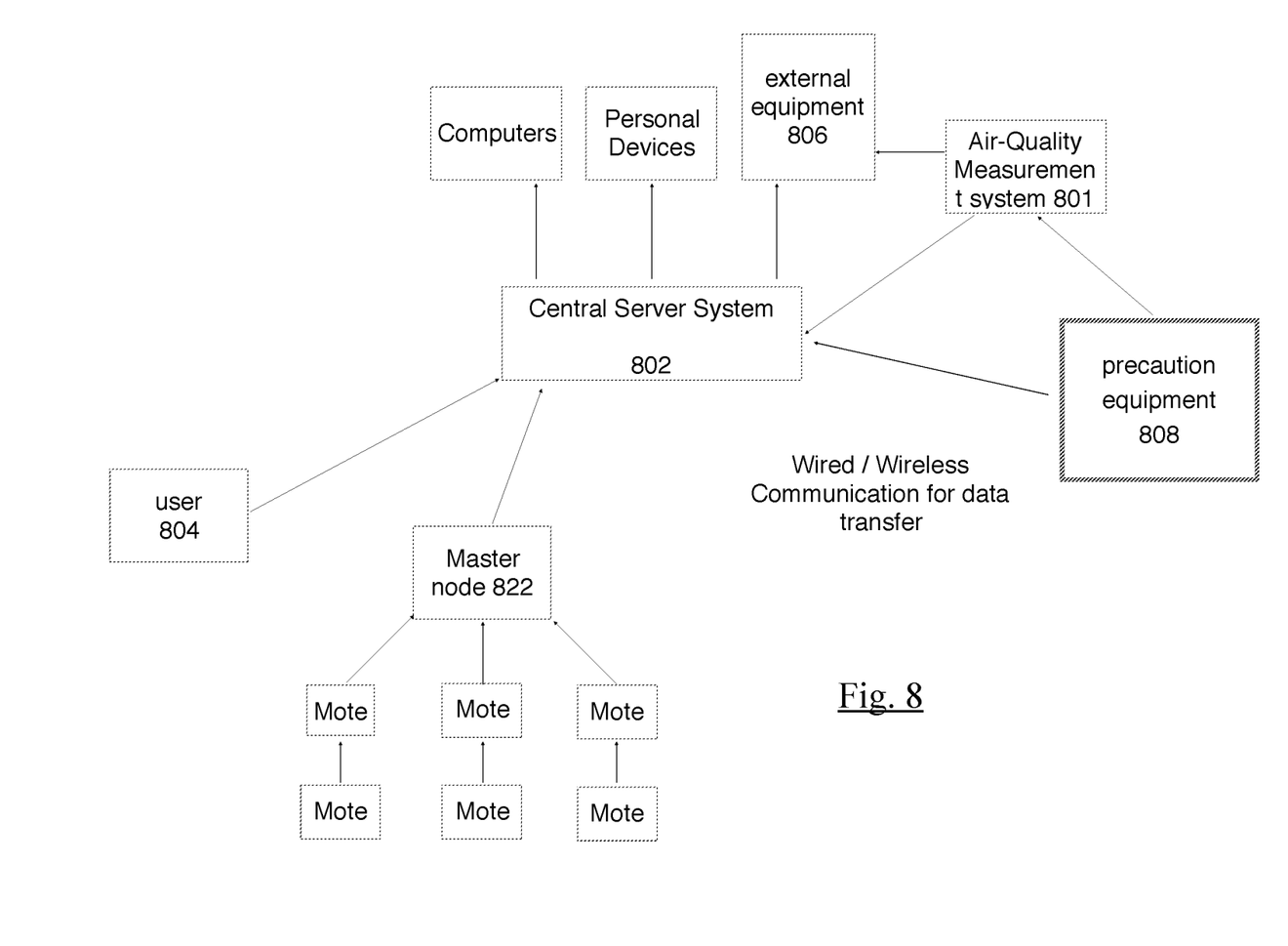
FIG. 8 illustrates an ecosystem for the air-quality measurement, control and monitoring as per an embodiment herein.

An ecosystem for air quality measurement and monitoring as per an embodiment herein may be as shown in FIG. 8. It may comprise of an air quality measurement system 801 connected with a central server system 802. The connection may be wired or wireless.

A user 804 may access the central server system 802 for accessing the air quality measurement system 801. This may allow for remote access to the results of the measurement as well as remote configuration. The central server system 802 may also be configured to install, check or update the software or firmware available in the air quality measurement system 801. A master node 822 may be provided that may have access to multiple air quality measurement units 844a-844g. This provides for measurement of various readings at the master node 822 and communicating with the central server, with or without processing of the results.

In one embodiment, an external equipment 806 may also be provided connected to the central server system 802. This may provide for change in operation of an equipment such as for example air purifier or an air conditioner depending on the result of air quality measurement. External equipment related to air-pollution precaution 808 may also be used to warn against rise in pollution levels. In one embodiment the air quality measurement system 801 may communicate directly with equipments 808, 806. In another embodiment the central server 802 manages such communications and management of these devices. In one embodiment, the air quality measurement system may be configured to control the equipments such as for example air purifier and air conditioner. In another embodiment the central server may control these equipments such as for example air purifier and air conditioner.

J. Navigation Application

Figure 9:
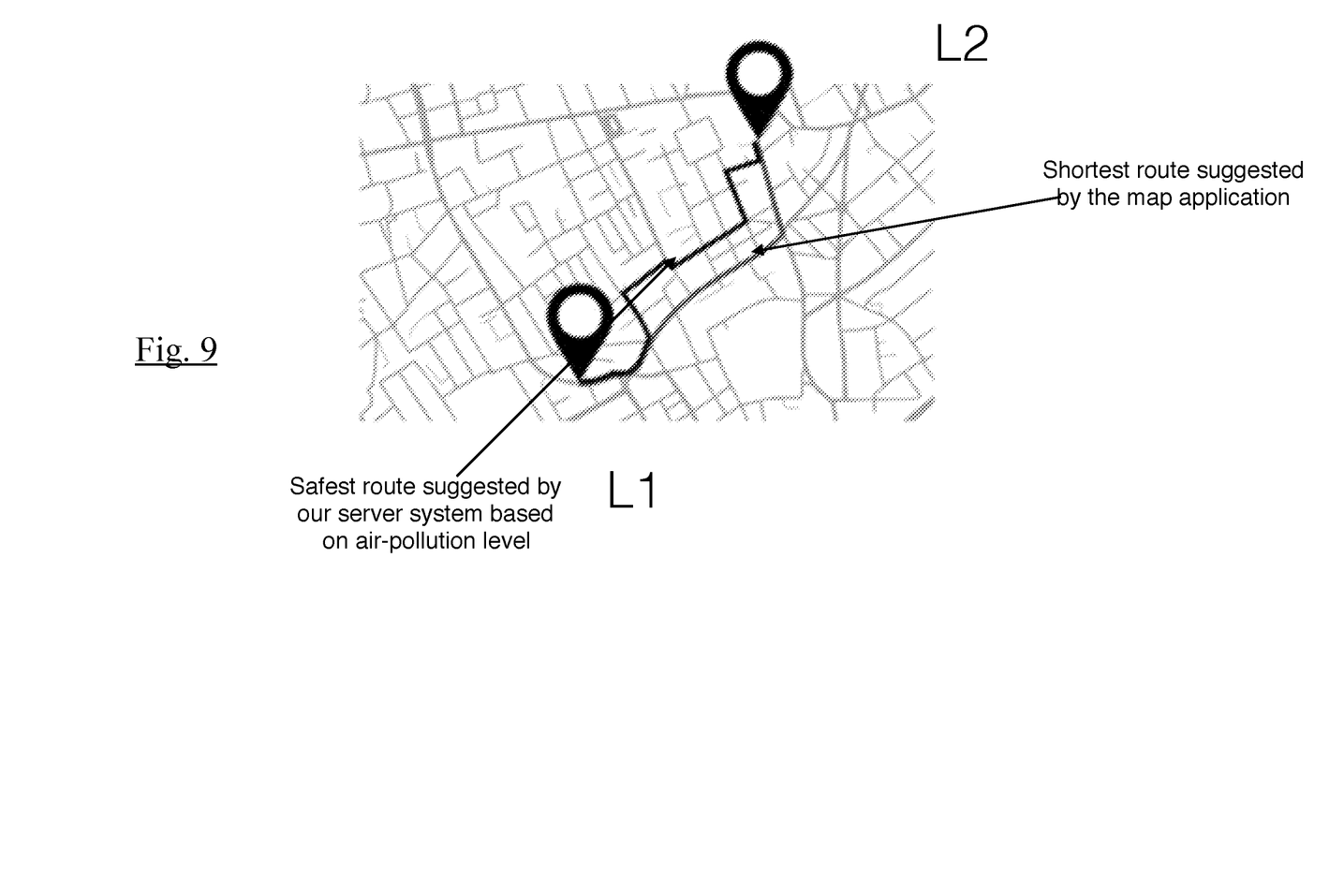
FIG. 9 illustrates a navigation map suggesting a navigation route depending on the air-quality measurement results in various parts of available routes, as per an embodiment herein.

A navigation system that suggests a route taking into account air quality measurement in various parts of available routes as per an embodiment may also be provided. The central server system 802 may be configured to collect various readings from air quality measurement systems installed in various parts of a geographical area. A user requesting navigation directions may be suggested a route depending on the data available with the central server, thereby avoiding areas with bad air quality.

Figure 10:
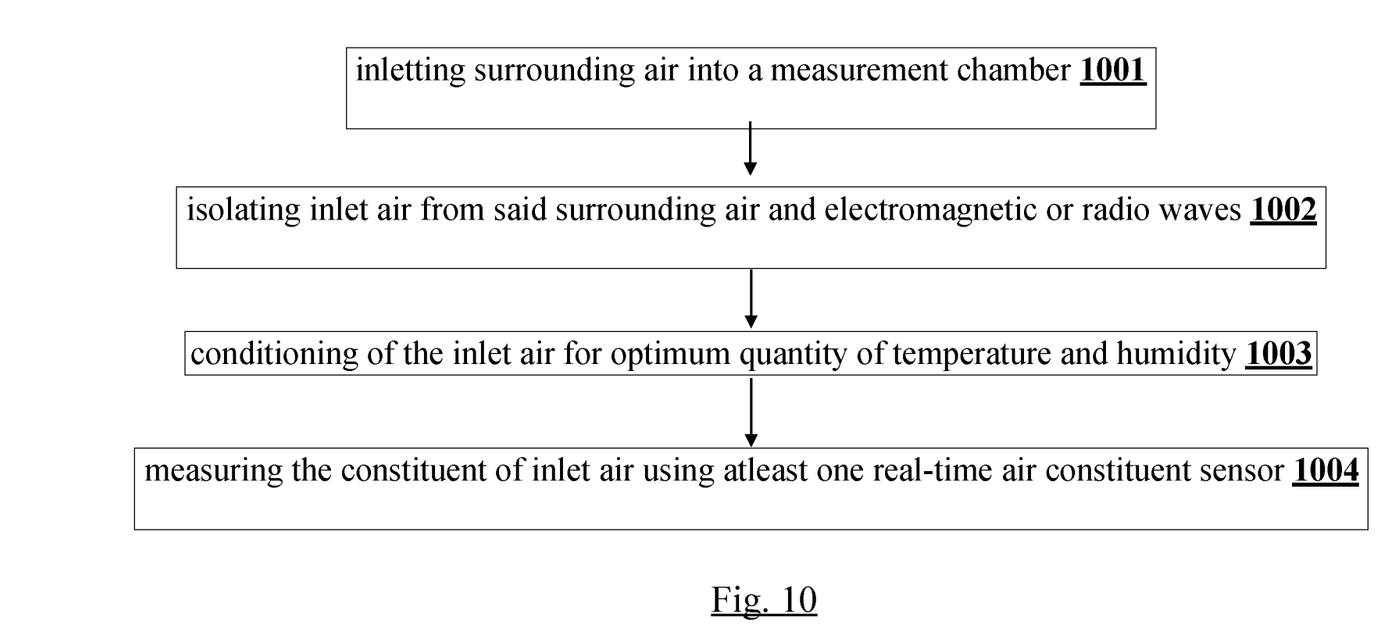
FIG. 10 illustrates a method for air-quality measurement as per an embodiment herein.

A method for air quality measurement as per an embodiment herein is as shown in FIG. 10. The method comprises the steps of inletting 1001 surrounding air into a measurement chamber. The inlet air may be isolated 1002 from the surrounding air and electromagnetic or radio waves. This can be achieved using various constructions of the inlet mechanism. The inlet air may be filtered for reducing the quantity of particulates in the part of the inlet air used for gas measurement. In the embodiment used for measuring the particulates, or the particulates and gas constituent in together, the filtration step may be skipped. Conditioning 1003 of the filtered inlet air for optimum quantity of temperature and humidity may take place before measurement. In one embodiment this may be done using an air-conditioning system including a humidifier and/or a dehumidifier and a temperature control unit such as for example a heating and/or cooling element. The conditioned air may be measured for identifying 1004 the quantity or presence of constituents of the conditioned air. The sensors used for measurement may be real time sensors working on Federal reference method (FRM) or Federal equivalent method (FEM) for measurement of for measuring the concentration of an air pollutant. The conditioned air may then be let out into the surrounding air.

A protective coating 222 on inner surface throughout the apparatus used for measurement may be provided to avoid radio wave/electromagnetic interference. Further, an inner coating 232 of fume-less material such as for example glass, may be provided along the inner surface of gas measurement chamber, thereby improving accuracy.

The instantaneous isolation of surrounding or outside air and the air being used for measurement improves the accuracy of the measurement.

We claim:

1. An air constituent measurement apparatus for measuring the constituents of inlet air, comprising:
    a measurement chamber;
    an air conditioning system configured to maintain the temperature and humidity of the inlet air in the measurement chamber;
    an inlet separator, wherein the inlet separator separates surrounding air and the inlet air, to isolate the surrounding air from the inlet air, and intermittently control the flow of the surrounding air into the measurement chamber;
    at least one real-time sensor configured to measure a constituent in the constituents of the inlet air;
    an outlet separator, wherein the outlet separator separates the inlet air and the surrounding air, to isolate the inlet air from the surrounding air, and intermittently control the flow of the inlet air into the surrounding air;
    a hollow housing assembly having a top face angled with respect to a ground and a bottom face depressed into the housing, thereby providing a bottom portion including cladding and an area for placement of the measurement chamber; and
    a solar panel installed on the top face; at least one hole on the cladding; a ventilation cutout on at least one face of the housing assembly allowing outflow of air from inside of the hollow housing assembly through natural or forced draft into the surrounding air.

2. The air constituent apparatus as in claim 1, further comprising an inner coating for reducing inlet of fumes caused by chamber construction material into the measurement chamber and surface absorption of various gases present in the inlet air by the chamber construction material.

3. The air constituent apparatus as in claim 1, wherein measurement consisting essentially of detection of the constituents of inlet air comprising particulates and gases.

4. The air constituent apparatus as in claim 1, further comprising:
    a protective coating for reducing the effect of at least one of: electromagnetic and radio waves, in the measurement chamber.

5. An air constituent measurement apparatus for measuring the constituents of inlet air, comprising:
    a gas measurement chamber and a particulate measurement chamber;
    an air conditioning system in the particulate measurement chamber configured to maintain the temperature and humidity of the inlet air in the particulate measurement chamber and the gas measurement chamber;
    an inlet separator for the gas measurement chamber, wherein the inlet separator separates surrounding air and the inlet air to isolate the surrounding air from the inlet air and intermittently control the flow of surrounding air into the gas measurement chamber;
    at least one real-time gas sensor configured to measure a gas in the constituents of the inlet air;
    an outlet separator for the gas measurement chamber, wherein the outlet separator separates inlet air and the surrounding air to isolate the inlet air from the surrounding air and intermittently control the flow of the inlet air into a surroundings;
    an inlet separator for the particulate measurement chamber, wherein the inlet separator separates surrounding air and the inlet air to isolate the surrounding air from the inlet air and intermittently control the flow of surrounding air into the particulate measurement chamber;
    at least one real-time particulate sensor configured to measure a particulate constituent of the inlet air;
    an outlet separator for the particulate measurement chamber, wherein the outlet separator separates inlet air and the surrounding air to isolate the inlet air from the surrounding air and intermittently control the flow of the inlet air into the surrounding air;
    a hollow housing assembly having a top face at an angle with respect to a ground and a bottom face depressed into the housing thereby providing a bottom portion including cladding and an area for placement of the measurement chambers; and
    a solar panel installed on the top face; at least one hole on the cladding; a ventilation cutout on at least one face of the housing assembly allowing outflow of air from inside of the hollow housing assembly through natural or forced draft into the surrounding air.

6. The air constituent measurement apparatus as in claim 5, further comprising: a filtration mechanism in the gas measurement chamber, configured to filter particulates from entering the gas measurement chamber.

7. The air constituent apparatus as in claim 5, further comprising an inner coating for reducing inlet of fumes caused by chamber construction material into the measurement chamber, and surface absorption of various gases present in the inlet air by the chamber construction material.

8. The air constituent apparatus as in claim 5, wherein measurement consisting essentially of detection, of the constituents of inlet air comprising particulates and gases.

9. The air constituent apparatus as in claim 5, wherein the at least one real-time gas sensor is facing a ground thereby avoiding the deposition of dust particles on the sensors.

10. The air constituent apparatus as in claim 5, wherein the particulate inlet separator is located at an angle with respect to a ground and configured to allow passage of the surrounding air moving in a direction parallel to the ground.

11. The air constituent measurement apparatus as in claim 5, further comprising:
    a protective coating for reducing the effect of at least one of electromagnetic and radio waves, in the gas measurement chamber and the particulate measurement chamber.

12. The air constituent apparatus as claimed in claim 5, wherein the particulate measurement chamber comprises the inlet separator with an opening that gradually reduces in area with a narrower opening into the particulate measurement chamber to cause venturi effect and the outlet separator comprises an opening that gradually increases in area with a narrower opening into a particulate measurement chamber to cause reverse venturi effect, wherein the at least one real-time particulate measurement sensor are placed on an upper wall of the apparatus and wherein the apparatus comprises an electronics system which is isolated from the particulate chamber with the help of an electronics system partition.

13. A method for air constituent measurement comprising the steps of:
    inletting surrounding air into a measurement chamber;
    isolating inlet air from said surrounding air;
    conditioning of the inlet air for optimum quantity of temperature and humidity prior to measurement of the constituent of inlet air;
    measuring the constituent of inlet air using at least one real-time air constituent sensor;
    separating inlet air and the surrounding air to isolate the inlet air from the surrounding air and intermittently control the flow of the inlet air into the surrounding air;
    placing the said measurement chamber in a hollow housing assembly having a top face at an angle with respect to a ground and a bottom face depressed into the housing thereby providing a bottom portion including cladding and an area for placement of the measurement chamber; and
    receiving power in the said measurement chamber using a solar panel installed on the top face; at least one hole on the cladding; a ventilation cutout on at least one face of the housing assembly allowing outflow of air from inside of the hollow housing assembly through natural or forced draft into the surrounding air.

14. The method for air constituent measurement as in claim 13 further comprising the step of:
    isolating inlet air from electromagnetic waves or radio waves.

* * * * *